United States Patent [19]

Hamprecht et al.

[11] 4,363,651
[45] Dec. 14, 1982

[54] 4H-3,1-BENZOXAZINE DERIVATIVES AND THEIR USE FOR CONTROLLING UNDESIRED PLANT GROWTH

[75] Inventors: Gerhard Hamprecht, Weinheim; Bruno Wuerzer, Otterstadt, both of Fed. Rep. of Germany

[73] Assignee: BASF Aktiengesellschaft, Fed. Rep. of Germany

[21] Appl. No.: 305,860

[22] Filed: Sep. 25, 1981

[30] Foreign Application Priority Data

Oct. 8, 1980 [DE] Fed. Rep. of Germany ....... 3037970

[51] Int. Cl.$^3$ .................... C07D 265/22; A01N 43/86
[52] U.S. Cl. .......................................... 71/88; 544/92
[58] Field of Search ............................. 544/92; 71/88

[56] References Cited

U.S. PATENT DOCUMENTS 3,232,736  2/1966  Seefelder .............................. 71/2.5
3,357,977  12/1967  Errede .................................. 544/92
3,989,698  11/1976  Jacobs et al. ......................... 544/92
4,315,766  2/1982  Hamprecht et al. ................... 544/92

FOREIGN PATENT DOCUMENTS 648259  4/1964  Belgium .
1670375  11/1970  Fed. Rep. of Germany .
2556590  9/1976  Fed. Rep. of Germany .

Primary Examiner—Norma S. Milestone
Attorney, Agent, or Firm—Keil & Witherspoon

[57] ABSTRACT 4H-3,1-Benzoxazine derivatives of the formula

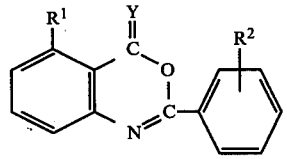

where $R^1$, $R^2$ and Y have the meanings given in the description, and their use for controlling undesired plant growth.

8 Claims, No Drawings

4H-3,1-BENZOXAZINE DERIVATIVES AND THEIR USE FOR CONTROLLING UNDESIRED PLANT GROWTH

The present invention relates to 4H-3,1-benzoxazine derivatives, to herbicides which contain these compounds as active ingredients, and to a process for controlling undesired plant growth by means of these compounds.

Substituted 4H-3,1-benzoxazin-4-ones are known as intermediates for the synthesis of pharmacologically active compounds (cf. German Laid-Open Applications DOS Nos. 1,670,375 and 2,556,590). Further, Belgian Pat. No. 648,259 discloses that halogen-substituted 4H-3,1-benzoxazin-4-ones, which carry an unsubstituted or substituted phenyl radical in the 2-position, have a herbicidal action. However, this last-mentioned publication only describes unsubstituted 4H-3,1-benzoxazine derivatives.

We have found that 4H-3,1-benzoxazine derivatives of the formula I

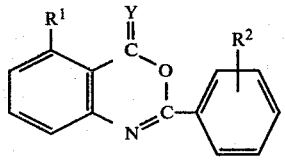
(I)

where Y is oxygen or sulfur, and $R^1$ is halogen if $R^2$ is halogen in the m- or p-position, or $R^1$ is methyl if $R^2$ is fluorine, trifluoromethyl, trifluoromethoxy or chlorodifluoromethoxy in the m-position, or $R^1$ is nitro if $R^2$ is trifluoromethoxy or chlorodifluoromethoxy, have a herbicidal action, coupled with good toleration by a range of crops.

In formula I, $R^1$ is, for example, fluorine, chlorine, bromine, iodine, nitro or methyl, and $R^2$ is, for example, fluorine, chlorine, bromine, iodine, trifluoromethyl, trifluoromethoxy or chlorodifluoromethoxy.

Preferred compounds of the formula I are those where Y is oxygen and $R^1$ is halogen, especially fluorine or chlorine, whilst $R^2$ is halogen, especially fluorine or chlorine, in the m- or p-position of the phenyl ring.

The 4H-3,1-benzoxazine derivatives of the formula I may be obtained by reacting a substituted anthranilic acid of the formula II

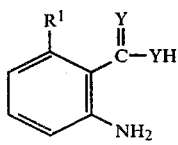
(II)

where $R^1$ and Y have the above meanings, with not less than a two-fold molar excess of a carboxylic acid halide of the formula III

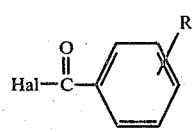
(III)

where $R^2$ has the above meanings and Hal is halogen, especially fluorine, chlorine or bromine, in an aromatic tertiary amine as the solvent, at from 10° to 60° C.

If 6-chloroanthranilic acid and 3-fluorobenzoyl chloride are used as starting materials, the course of the reaction can be represented by the following equation:

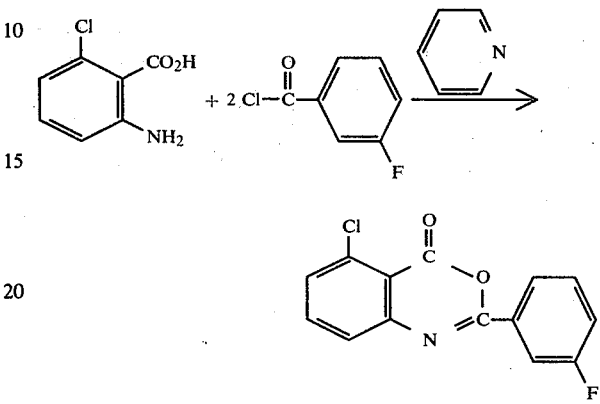

Advantageously, a two-fold excess of the carboxylic acid halide of the formula III is run into a solution of the anthranilic acid of the formula II in from 5 to 25 moles of an aromatic amine per mole of anthranilic acid, at from 10° to 60° C., and the mixture is then stirred for 30 minutes, at 25° C. (J. Chem. Soc. (C) (1968), 1593). The mixture can then be worked up by stirring it into ice water and filtering off the precipitate formed. The reaction can, alternatively, be carried out by taking the carboxylic acid halide of the formua III and adding the anthranilic acid.

Examples of suitable aromatic tertiary amines are pyridine, α-, β- and γ-picoline, lutidine, quinoline and acridine.

The benzoxazine derivatives of the formula I can also be obtained by reacting a substituted anthranilic acid of the formula II

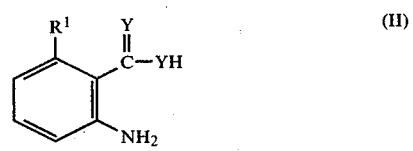
(II)

where $R^1$ and Y have the above meanings, or an alkali metal salt or alkaline earth metal salt of this anthranilic acid, with about the stoichiometric amount of a carboxylic acid halide of the formula III

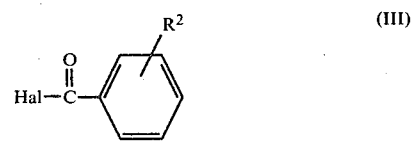
(III)

where $R^2$ has the meanings given in claim 1 and Hal is halogen, in an inert organic solvent or in water, in the presence or absence of an acid acceptor, at from 0° to 60° C., to give a carboxamide of the formula IV

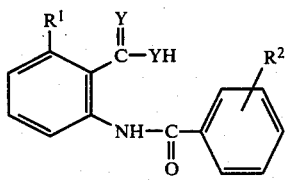

where $R^1$, $R^2$ and Y have the above meanings, and then cyclizing the carboxamide in the presence of a dehydrating agent at from 30° to 150° C.

If 3-trifluoromethylbenzoyl fluoride and 6-methylanthranilic acid are used as starting materials, the course of the reaction can be represented by the following equation:

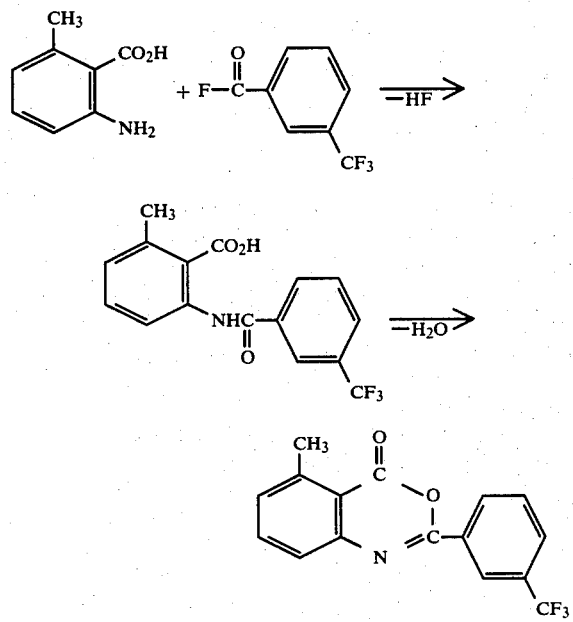

Suitable inert solvents for this reaction are hydrocarbons, eg. naphtha, gasoline, toluene, pentane, hexane, cyclohexane and petroleum ether, halohydrocarbons, eg. methylene chloride, chloroform, carbon tetrachloride, 1,1- and 1,2-dichloroethane, 1,1,1- and 1,1,2-trichloroethane, chlorobenzene, o-, m- and p-dichlorobenzene and o-, m- and p-chlorotoluene, nitrohydrocarbons, eg. nitrobenzene, nitroethane and o-, m- and p-chloronitrobenzene, nitriles, eg. acetonitrile, butyronitrile and isobutyronitrile, ethers, eg. diethyl ether, di-n-propyl ether, tetrahydrofuran and dioxane, esters, eg. ethyl acetoacetate, ethyl acetate or isobutyl acetate, and amides, eg. formamide, methylformamide and dimethylformamide.

The acid acceptor used can be any of the conventional acid-binding agents. Preferred categories of these are alkali metal hydroxides, alkali metal carbonates and tertiary organic bases. Examples of particularly suitable acid acceptors are sodium hydroxide, sodium carbonate, sodium bicarbonate, triethylamine, pyridine, trimethylamine, α-, β- and γ-picoline, lutidine, N,N-dimethylaniline, N,N-dimethylcyclohexylamine, quinoline, tri-n-propylamine and tri-n-butylamine. The acid acceptor is advantageously employed in an amount equivalent to the carboxylic acid halide of the formula III.

Suitable dehydrating agents are symmetrical and mixed carboxylic acid anhydrides, such as acetic anhydride, propionic anhydride, butyric anhydride, formic-acetic anhydride, formic-propionic anhydride and acetic-propionic anhydride, as well as dicyclohexylcarbodiimide or thionyl chloride. The cyclization is carried out with from 1 to 10 moles of dehydrating agent per mole of carboxamide of the formula IV.

The starting materials of the formulae II and III are employed in about the stoichiometric ratio, ie. with not more than 10% deficiency or 10% excess of the starting material of the formula III in relation to the starting material of the formula II.

Advantageously, the process is carried out by running the carboxylic acid halide of the formula III and the equivalent amount of acid acceptor, from two feeds, into an about equivalent amount of the anthranilic acid of the formula II, or of a salt thereof, in an inert organic solvent or in water respectively, at from 0° to 60° C. The mixture is then stirred for 15 minutes at room temperature. Thereafter, it is evaporated down if necessary, acidified with 5 N hydrochloric acid whilst hot, cooled, and filtered (J. Org. Chem. 2 (1944), 396), giving a N-acyl-2-aminobenzoic acid. The latter can then be cyclized to the desired 4H-3,1-benzoxazine by stirring, in the presence of from 5 to 10 moles of carboxylic acid anhydride (per mole of benzoxazine) as the dehydrating agent; the carboxylic acid anhydride can be, for example, acetic anhydride, and the acetic acid formed may or may not be distilled off whilst the mixture is being stirred. For working up, excess dehydrating agent is removed under reduced pressure and, if desired, the product is purified by recrystallization. Instead of taking the anthranilic acid and adding the carboxylic acid halide, the converse procedure can be followed. If dicyclohexylcarbodiimide or thionyl chloride is used as the dehydrating agent, from 1 to 4 moles of these compounds are employed per mole of reactants in the cyclization.

To isolate the 4H-3,1-benzoxazine derivatives of the formula I from the reaction mixture, the latter can be treated with water, dilute alkali or dilute acid to remove by-products, such as unconverted anthranilic acid, acid chloride or base hydrochloride, and then dried and evaporated down. If desired, the end products can be purified by recrystallization or chromatography.

The Examples which follow illustrate the preparation of the novel 4H-3,1-benzoxazine derivatives of the formula I. Parts by weight bear the same relation to parts by volume as that of the kilogram to the liter.

EXAMPLE 1

Preparation of 2-(3'-fluorophenyl)-5-chloro-4H-3,1-benzoxazin-4-one (a) 15.9 parts of 3-fluorobenzoyl chloride and 10.1 parts of triethylamine are introduced simultaneously, from 2 feeds, into a solution of 17.1 parts of 6-chloroanthranilic acid in 200 parts of methylene chloride at from 25° to 30° C. The reaction mixture is subsequently stirred for 30 minutes, and is extracted once with 1 N hydrochloric acid and then with water. The organic solution is dried and concentrated, giving 29 parts of N-(3'-fluorobenzoyl)-6-chloroanthranilic acid of melting point 216°–219° C.; yield: 98.6% of theory.

(b) 29 parts of N-(3'-fluorobenzoyl)-6-chloroanthranilic acid in 250 parts of acetic anhydride are stirred under reflux for 2½ hours. The mixture is evaporated down under reduced pressure, the residue is taken up in methylene chloride and this solution is washed with twice 100 parts by volume of 0.5 N sodium hydroxide solution and then with water. Thereafter, the solution is chromatographed on neutral alumina, giving 23.6 parts of 2-(3'-fluorophenyl)-5-chloro-4H-3,1-benzoxazin-4-one, of melting point 123°–125° C.; yield: 86.7% of theory.

EXAMPLE 2

Preparation of 2-(4'-fluorophenyl)-5-chloro-4H-3,1-benzoxazin-4-one (a) 17.5 parts of 4-fluorobenzoyl chloride and 14 parts of N,N-dimethylcyclohexylamine are introduced simultaneously, from 2 feeds, into a solution of 17.1 parts of 6-chloroanthranilic acid in 230 parts of ethyl acetate at from 10° to 20° C., and the mixture is then stirred for 20 minutes at 30° C. Thereafter, the reaction mixture is washed once with 1 N hydrochloric acid and then with water, a colorless precipitate being formed. The latter is dissolved in ethyl acetate, and the organic phase is again washed with 1 N hydrochloric acid and then with water, dried over magnesium sulfate and evaporated down; 29 parts of N-(4'-fluorobenzoyl)-6-chloroanthranilic acid, of melting point 228°–233° C., are obtained.

(b) 15.5 parts of thionyl chloride are added to a suspension of 29 parts of N-(4'-fluorobenzoyl)-6-chloroanthranilic acid in 250 parts of 1,2-dichloroethane at room temperature, and the mixture is then stirred for one hour under reflux. Thereafter, it is evaporated down and the residue is taken up in methylene chloride; this solution is extracted once with water, and then with twice 100 parts by volume of 0.5 N sodium hydroxide solution. Thereafter, it is dried, chromatographed on neutral alumina and evaporated down, 22.5 parts of 2-(4'-fluorophenyl)-5-chloro-4H-3,1-benzoxazin-4-one, of melting point 159°–162° C., being isolated; yield: 82.7%.

EXAMPLE 3

Preparation of 2-(3'-trifluoromethyl)-5-methyl-4H-3,1-benzoxazin-4-one (a) 15.4 parts of 3-trifluoromethylbenzoyl fluoride are added to a stirred mixture of 13.3 parts of 6-methylanthranilic acid and 16.3 parts of tri-n-butylamine in 250 parts of 1,2-dichloropropane at 20°–25° C., and stirring is continued for 20 minutes. The precipitate formed is filtered off and washed with 1 N hydrochloric acid and then with water; the organic filtrate is washed similarly, dried and evaporated down. 27 parts of N-(3'-trifluoromethylbenzoyl)-6-methylanthranilic acid, of melting point 198°–204° C., are obtained.

(b) 27 parts of N-3'-trifluoromethylbenzoyl-6-methylanthranilic acid in 200 parts of acetic anhydride are stirred under reflux for two hours. The mixture is then evaporated down under reduced pressure, the residue is taken up in methylene chloride and this solution is washed with twice 100 parts by volume of 0.5 N sodium hydroxide solution and then with water. The solution is then chromatographed on neutral alumina, giving 23 parts of 2-(3'-trifluoromethyl)-5-methyl-4H-3,1-benzoxazin-4-one, of melting point 120°–123° C.; yield: 89.6%.

The following are examples of 4H-3,1-benzoxazine derivatives of the formula I which can be prepared by a similar method:

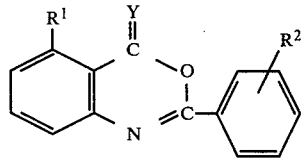

| No. | R[1] | R[2] | Y | m.p. [°C.] |
|---|---|---|---|---|
| 4 | Cl | m-Cl | O | 170–173 |
| 5 | Cl | m-F | S | |
| 6 | Cl | p-Cl | O | 208–210 |
| 7 | Cl | p-F | S | |
| 8 | Cl | p-I | O | 188–191 |
| 9 | Cl | m-Br | O | 206–208 |
| 10 | Cl | p-Br | O | 202–206 |
| 11 | F | m-F | O | 135–138 |
| 12 | F | m-F | S | |
| 13 | F | m-Cl | O | 182–184 |
| 14 | F | p-Cl | O | 199–201 |
| 15 | F | p-F | O | 192–194 |
| 16 | F | p-F | S | |
| 17 | CH$_3$ | m-CF$_3$ | S | |
| 18 | CH$_3$ | m-O—CF$_3$ | O | 90–93 |
| 19 | CH$_3$ | m-O—CF$_2$Cl | O | 83–86 |
| 20 | CH$_3$ | m-OCF$_2$Cl | S | |
| 21 | CH$_3$ | m-F | O | 125–128 |
| 22 | NO$_2$ | m-O—CF$_3$ | O | 103–105 |
| 23 | NO$_2$ | m-O—CF$_2$Cl | O | 123–126 |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of the compound of Example 1 is mixed with 10 parts by weight of N-methyl-α-pyrrolidone. A mixture is obtained which is suitable for application in the form of very fine drops.

II. 10 parts by weight of the compound of Example 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

III. 20 parts by weight of compound no. 4 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

IV. 20 parts by weight of compound no. 11 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 6 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 13 is intimately mixed with 95 parts by weight of particulate kaolin. A dust is obtained containing 5% by weight of the active ingredient.

VII. 30 parts by weight of compound no. 14 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 15 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of various representatives of the 4H-3,1-benzoxazine derivatives of the formula I on the growth of unwanted plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species.

In the preemergence treatment, the active ingredients were applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which had been sown directly in the pots and grown there were selected, or plants which had been grown separately as seedlings and transplanted to the experiment vessels a few days before treatment. The amount of active ingredient applied in this treatment varied, depending on the active ingredient, and was either 0.5 or 1.0 kg/ha. The comparative agent employed was 2-phenyl-4H-3,1-benzoxazin-4-one (A) (Belgian 648,259), at a rate of 1.0 kg/ha. No cover was placed on the vessels in this treatment.

The pots were set up in the greenhouse—species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The following plants were employed in the experiments: Arachys hypogaea, Avena sativa, Cassia tora, Centaura cyanus, Chenopodium spp., Chrysanthemum spp., Datura stramonium, Desmodium tortuosum, Euphorbia geniculata, Galium aparine, Gossypium hirsutum, Ludwigia spp., Mercurialis annua, Oryza sativa, Sinapis alba, Solanum nigrum, Triticum aestivum and Zea mays.

In investigations into the herbicidal action on preemergence application in the greenhouse at a rate of 3.0 kg/ha, novel compounds nos. 11, 22 and 23 exhibit a good herbicidal action and are well tolerated by oats (representing cereals).

In investigations into the selective herbicidal action on postemergence application in the greenhouse, active ingredient no. 22 exhibits, at 1.0 kg/ha, and no. 23 at 0.5 kg/ha, a better herbicidal action than prior art active ingredient A at 1.0 kg/ha, and is also better tolerated by cotton. Active ingredients nos. 1 and 11, in selective weed control on postemergence application in the greenhouse, also have, at 1.0 and 0.5 kg/ha, a very good herbicidal and selective action.

In further investigations into the selective herbicidal action on postemergence application in the greenhouse, active ingredients nos. 18 and 19 are, at 1.0 kg/ha, extremely well tolerated by wheat and have a very good action on Solanum nigrum (representing weeds).

When applied postemergence in the greenhouse at 3.0 kg/ha, active ingredients nos. 2 and 15 reveal a considerable herbicidal action on broadleaved weeds, especially Galium aparine, and are excellently tolerated by cereals, e.g., oats.

If certain crop plants tolerate, on leaf treatment, the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

In view of the good tolerance of the active ingredients and the many application methods possible, the active ingredients according to the invention, and herbicidal agents containing them, may be used in a very wide range of crops for removing unwanted plants. The application rates may vary between 0.1 and 15 kg of active ingredient per hectare and more, but are preferably from 0.5 to 3.5 kg/ha. They depend on the object to be achieved, the growth stage of the unwanted plants, and the time of the year.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape seed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (N. rustica) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. *vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (V. *unguiculata*) | cow peas |
| *Vitis vinifera* | grapes |
| *Zea mays* | Indian corn, sweet corn, maize |

To increase the spectrum of action and to achieve synergistic effects, the novel 4H-3,1-benzoxazin-4-ones may be mixed and applied together with numerous representatives of other herbicidal or growth-regulating active ingredient groups. Examples of suitable mixture components are diazines, other 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:
5-amino-4-chloro-2-phenyl-3(2H)-pyridazinone 5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
4,5-dimethoxy-2-(3-α,α,β-trifluoro-β-bromoethoxyphenyl)-3-(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
methyl-N-dichlorofluoromethylsulfenyl-(3-(N'-dichlorofluoromethylsulfenyl-N'-phenylcarbamoyloxy)-phenyl)-carbamate
methyl-N-dichlorofluoromethylsulfenyl-(3-(N'-dichlorofluoromethylsulfenyl-N'-3-methylphenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
ethyl 4-(4'-trifluoromethylphenoxy)-pentene-2-carboxylate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
N-benzyl-N-isopropyl-trimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyl-trifluoromethanesulfone anilide
5-acetamido-4-methyl-trifluoromethanesulfone anilide
N-4-methyl-5-(trifluoromethyl)-sulfonylamino-phenylacetamide 2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2-chloro-4-trifluoromethylphenyl-3'-ethoxycarbonyl-4'-nitrophenyl ether
2-chloro-4-trifluoromethylphenyl-3'-(2-fluoroethoxy)-4'-nitrophenyl ether
2-chloro-4-trifluoromethylphenyl-3'-ethoxycarbonylmethylthio-4'-nitrophenyl ether
2-chloro-4-trifluoromethylphenyl-3'-methoxycarbonyl-4'-nitrophenyl ether
2,4,6-trichlorophenyl-3'-ethoxycarbonyl-methylthio-4'-nitrophenyl ether
2,4-dichlorophenyl-3'-methoxycarbonyl-4'-nitro-phenyl ether
2,4-dichlorophenyl-3'-carboxy-4'-nitrophenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(3-α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
1-(4-benzyloxyphenyl)-3-methyl-3-methoxyurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
1-acetyl-3-anilino-4-methoxycarbonyl-5-methyl-pyrazole
3-anilino-4-methoxycarbonyl-5-methylpyrazole
3-tert-butylamino-4-methoxycarbonyl-5-methyl-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
methyl 2-[4-chlorophenoxymethyl)-phenoxy]-propionate
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
2-[1-(2,5-dimethylphenyl)-ethylsulfonyl]-pyridine-N-oxide
2-(3'-trifluoromethylphenyl)-4H-3,1-benzoxazin-4-one
2-(2-thienyl)-4H-3,1-benzoxazin-4-one
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl-4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-α,α,β-trifluoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-yiridine
1(-4-[2-(4-methylphenyl)-ethoxy]-phenyl-3-methyl-3-methoxyurea
2,6-dimethyl-N-(pyrazol-1-yl-methylenoxymethyl)-2-chloroacetanilide
2-methyl-6-ethyl-N-(pyrazol-1-yl-methylenoxmethyl)-2-chloroacetanilide
2-methyl-6-ethyl-N-(pyrazol-1-yl-ethylenoxymethyl)-2-chloroacetanilide
1-(-2,4-dichlorophenoxypropionic acid)-3-(O-methylcarbamoyl)-anilide
1-(-2-bromo-4-chlorophenoxypropionic acid)-3-(O-methylcarbamoyl)-anilide
methyl-N-dichlorofluoromethylsulfenyl-(3-N'-dichlorofluoromethylsulfenyl-N'-phenylcarbamoyl-oxy)-phenyl)-carbamate
methyl-N-dichlorofluoromethylsulfenyl-(3-(N'-dichlorofluoromethylsulfenyl-N'-3-methylphenylcarbamoyl-oxy)-phenyl)-carbamate
N-(pyrazol-1-yl-methyl)-pyrazol-1-yl-acetic acid-2,6-dimethylanilide
N-(pyrazol-1-yl-methyl)-1,2,4-triazol-1-yl-acetic acid-2,6-dimethylanilide
2-(3'-trifluoromethylphenyl)-4H-3,1-benzoxazin-4-one
2-(2-thienyl)-4H-3,1-benzoxazin-4-one
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino)-butylidene]-5,5-dimethylcyclohexane-1,3-dione (salts)
2-[1-(N-allyloxyamino)-butylidene]-5,5-dimethyl-4-methoxycarbonyl-cyclohexane-1,3-dione (salts).

It may also be useful to apply the mixtures according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies.

To initiate the herbicidal action, wetting agents, spreader-stickers and non-phytotoxic oils and oil concentrates may be added.

We claim:

1. A 4H-3,1-benzoxazine derivative of the formula

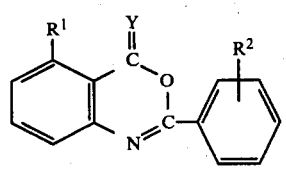
(I)

where Y is oxygen or sulfur, $R^1$ is halogen and $R^2$ is halogen in the m- or p-position.

2. A 4H-3,1-benzoxazine derivative of the formula I as set forth in claim 1, wherein Y is oxygen.

3. 2-(3'-Fluorophenyl)-5-chloro-4H-3,1-benzoxazin-4-one.

4. 2-(3'-Fluorophenyl)-5-fluoro-4H-3,1-benzoxazin-4-one.

5. A 4H-3,1-benzoxazine derivative of the formula

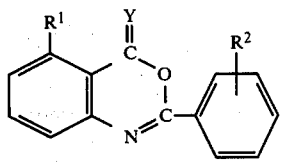
(I)

where Y is oxygen or sulfur, $R^1$ is methyl and $R^2$ is fluorine, trifluoromethyl, trifluoromethoxy or chlorodifluoromethoxy in the m-position.

6. A 4H-3,1-benzoxazine derivative of the formula (I)

where Y is oxygen or sulfur, $R^1$ is nitro and $R^2$ is trifluoromethoxy or chlorodifluoromethoxy.

7. A herbicide comprising inert additives and a 4H-3,1-benzoxazine derivative of the formula I as set forth in claim 1, 5 or 6.

8. A process for combating unwanted plant growth, wherein the plants and/or their location are treated with a herbicidally effective amount of a 4H-3,1-benzoxazine derivative of the formula I as set forth in claim 1, 5 or 6.

* * * * *